United States Patent [19]

Tomcufcik et al.

[11] Patent Number: 4,892,885

[45] Date of Patent: Jan. 9, 1990

[54] ESTERS OF (TRIARYLPHOSPHORANYLIDENE)CARBAMIC ACID FOR EFFECTING DIURESIS

[75] Inventors: Andrew S. Tomcufcik, Old Tappan; William B. Wright, Jr., Woodcliff Lake, both of N.J.; Walter E. Meyer, Suffern, N.Y.

[73] Assignee: American Cyanamid Company

[21] Appl. No.: 183,122

[22] Filed: Apr. 19, 1988

[51] Int. Cl.$^4$ .................... C07C 125/06; A61K 31/27
[52] U.S. Cl. ........................................ 514/478; 560/27
[58] Field of Search ........................... 560/27; 514/478

[56] References Cited

U.S. PATENT DOCUMENTS 3,136,801  6/1964  Hopkins ............................... 560/27

Primary Examiner—Mary C. Lee
Assistant Examiner—Robert C. Whittenbaugh
Attorney, Agent, or Firm—H. G. Jackson

[57] ABSTRACT

This disclosure describes novel esters of (triarylphosphoranylidene)carbamic acid which are useful as diuretic agents.

9 Claims, No Drawings

ESTERS OF (TRIARYLPHOSPHORANYLIDENE)CARBAMIC ACID FOR EFFECTING DIURESIS

SUMMARY OF THE INVENTION

This invention is concerned with new compounds of the formula:

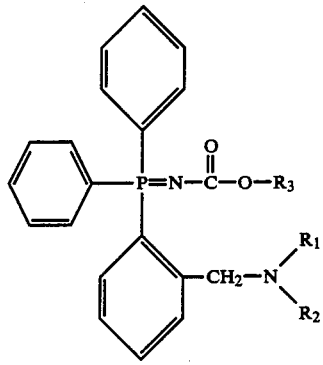

Formula I wherein $R_1$ and $R_2$ may be the same or different and are each individually hydrogen or lower alkyl having from one to four carbon atoms, where lower alkyl may include both straight chain and branched chain alkyl radicals; $R_1$ and $R_2$ taken together with their associated nitrogen is

where n is an integer from 4–6; and $R_3$ is lower alkyl having from one to four carbon atoms.

This invention is also concerned with a method for effecting diuresis and lowering plasma renin activity in mammals as well as pharmaceutical compositions of matter containing these compounds and with processes for the preparation of the compounds.

DETAILED DESCRIPTIONN OF THE INVENTION

In accordance with the present invention, there are provided novel methods of effecting diuresis and lowering plasma renin activity which comprise administering to said mammal a therapeutically effective amount of a compound selected from those of the above described formula I.

The compounds of formula I find utility as diuretics and cardiotonics in mammals and as such may be used as the drug of choice for the treatment of edema caused by cardiac, hepatic, pulmonary and renal diseases, as well as drug-induced fluid and salt retention. These compounds may also be useful as hypotensive agents upon chronic administration by virtue of their diuretic activity. As cardiotonic agents, these compounds may likewise be useful in the treatment of congestive heart failure.

The action of the currently available diuretics can be depicted by the following diagram:

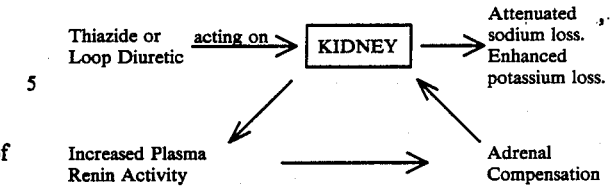

In contrast, the compounds of the present invention acting on the kidney lower plasma renin activity, thereby effecting non-attenuated sodium loss and minimal potassium loss, and preventing adrenal compensation.

```
Compounds of  acting on   KIDNEY   →  Non-attenuated
Formula I     ────────→                sodium loss.
                                       Minimal
                                       potassium loss.
                        ↓
              Decreased Plasma      →  No Adrenal
              Renin Activity           Compensation
```

The compounds of this invention may be prepared as described in the following flowcharts and text.

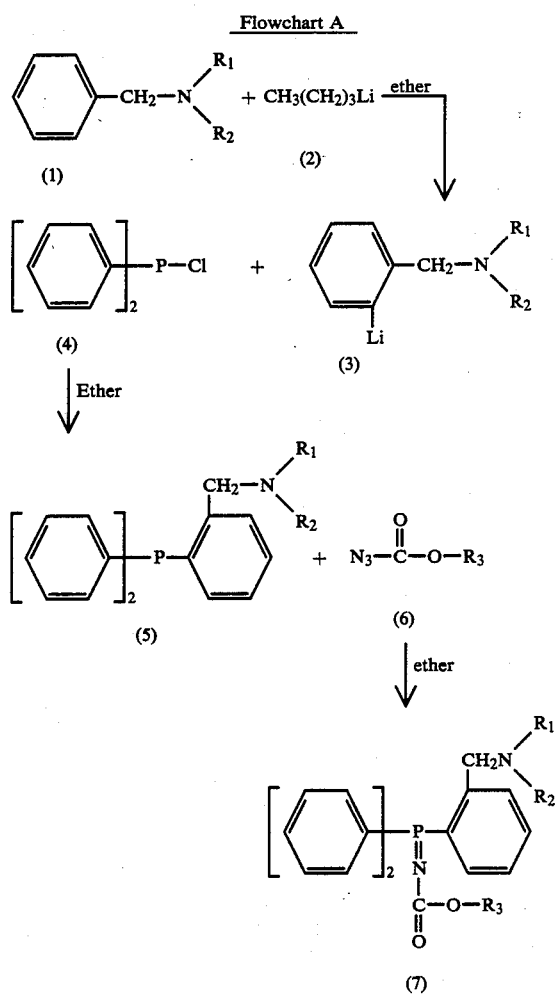

where $R_1$, $R_2$ and $R_3$ are as hereinabove defined.

In accordance with Flowchart A an N,N-substituted benzylamine (1) and diethyl ether are mixed under an inert atmosphere. Then butyl lithium (2) in hexane is added and the mixture is stirred for an effective time under nitrogen or argon to give the intermediate ortho lithium compound (3). A mixture of diphenylphosphine chloride (4) in ether is added dropwise and the reaction mixture is stirred for an effective time. Water is added and the organic layer is separated and extracted with a dilute acid such as hydrochloric acid. The combined acid extracts are made basic with 10% sodium hydroxide and extracted with a solvent such as ether. The extracts are dried and evaporated to give the 2-(diphenylphosphino)-N,N-substitutedbenzenemethanamine compound (5). The compound (5) is then reacted with a carbonazidate ester (6) in a solvent such as diethyl ether by allowing to stand for an effective time, about 48 hours, then repeatedly concentrating and treating with fresh ether, followed by refrigeration to obtain the desired products (7).

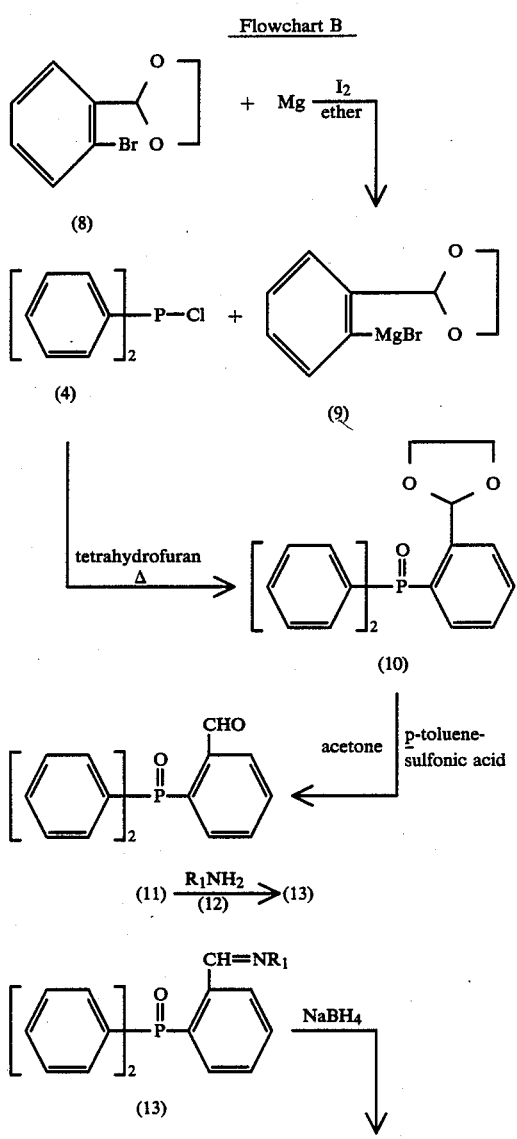

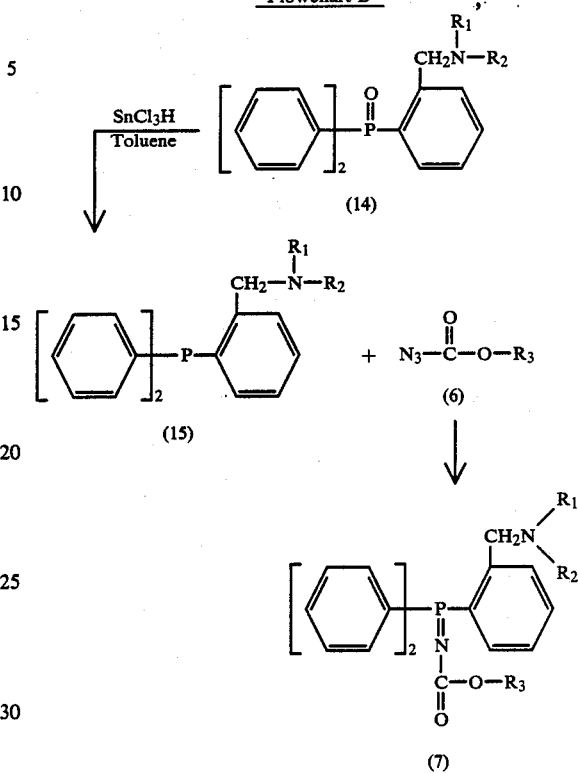

wherein $R_1$, $R_2$ and $R_3$ are as hereinabove defined.

In accordance with Flowchart B, 2-(o-bromophenyl)-1,3-dioxolane (8) is dissolved in ether and treated with magnesium, yielding 2-(o-bromomagnesiophenyl9-1,3-dioxolane (9). Treatment of this compound with diphenylphosphine chloride (4) in tetrahydrofuran solution leads to [2-(1,3-dioxolan-2-yl)phenyl]diphenylphosphine which under the conditions of the work-up procedure is converted to the phosphine oxide (10). Treatment of (10) with p-toluenesulfonic acid in acetone solution yields the benzaldehyde derivative (11). Subsequent reaction of (11) with an alkylamine (12) leads to the imino derivative (13) which upon reduction with sodium borohydride in ethanol gives the (o-alkylaminomethylphenyl)diphenylphosphine oxide (14). Reduction of (14) with trichlorosilane in refluxing toluene then gives the phosphine (15). Reaction of (15) with a carbonazidate ester (6) in a solvent such as ether then leads to the desired products (7).

It is generally preferred that the respective product of each process step described in the above reaction schemes be separated and/or isolated prior to its use as starting material for subsequent steps. Separation and isolation can be effected by any suitable purification procedure such as evaporation, crystallization, column chromatography, distillation, etc. Also it should be appreciated that reaction times, temperatures and mole ratios are within the skill of the art.

Inhibition of evoked increase of plasma renin activity was determined by the following test.

Compounds were tested for their ability to prevent drug-induced elevation of plasma renin activity (PRA) in conscious, male Wistar rats (180–200 g, Charles River Lab.). PRA elevation was induced by a combined oral provocative treatment (C) of hydrochlorothiazide (10 mg/kg) and 1-(3-benzoyl-3-mercapto-2-methylpropionyl)-L-proline, acetate (U.S. Pat. No. 4,226,775) (one mg/kg), prepared by compounding in a mortar and pestle with preboiled 3% starch suspension. This treatment provided the daily maximum PRA. The daily minimum PRA was obtained from rats given oral starch suspension (S) alone. The magnitude of drug effect on PRA elevation was ascertained from rats pretreated orally with test agent (D), at the indicated doeses, 30 minutes prior to administration of provocative treatment (C). The test agent was also compounded in preboiled 3% starch suspension. The dose volumes for both pretreatment and provocative treatment were 2 ml/kg. One hour after provocative treatment the rats were sacrificed by decapitation and the first 3 seconds of blood collected in two chilled vacutainer tubes containing 40 1 of 150 mg/ml tripotassium EDTA. The plasmas, which were obtained by centrifugation for 20 minutes at 4° C. and 3000 G, were incubated (one of each pair of 37° C., the other at 4° C.) at pH 6.8 in 50 mM phosphate buffer to produce angiotensin I. The incubates contained peptidase inhibitors to prevent angiotensin I degradation and the incubation buffer contained one mg/ml lysozyme (Sigma Grde III) uses as an antiabsorbant. The incubates were diluted 20 fold in cold 100 mM Tris buffer (pH adjusted to 7.4 with glacial acetic acid) also containing one mg/ml lysozyme, and then frozen. Diluted incubates were assayed within 3 days for angiotensin I content by radioimmunoassay according to a modification of the method of Haber, et al., J. Clin. Endocrin., 29, 1349–1355 (1969).

PRA is calculated as follows: PRA (mg AI/hour/ml plasma)=PRA 37° C.-PRA 4° C.

Percent inhibition of PRA elevation is calculated as follows:

$$\% \text{ Inhibition} = 100 \times \frac{[PRA(C) - PRA(D)]}{[PRA(C) - PRA(S)]}.$$

The results of this test on representative compounds of this invention appear in Table I.

TABLE I

Percent Inhibition of Plasma Renin Elevation

| Compound | Dose (mg/kg) | Average % Inhibition (No. of rats) |
|---|---|---|
| [[2-[(Dimethylamino) methyl]-phenyl] diphenylphosphoranylidene] carbamic acid, ethyl ester | 25 | 16(3) |
| [[2-[(Dimethylamino)methyl]-phenyl] diphenylphosphoranylidene] carbamic acid, methyl ester | 25 | 77(1) |

The diuretic activity of the compounds of this invention was also determined according to the method of Chan, P. S. and Poorvin, D., "Sequential method for combined screening antihypertensive and diuretic agents in the same spontaneously hypertensive rat." Clinical and Experimental Hypertension, 1(6), 817–830 (1979).

Male spontaneously hypertensive rats (SHR) of Okamoto strain, 16 weeks old, Taconic Farms Inc. were used in the test. These rats were kept on Purina laboratory chow and tap water ad libitum for 8 weeks before use. One male adult rat (about 300 g) was dosed by gavage with a test compound at 100 mg/kg together with 0.9 sodium chloride loading at 25 ml/mg at zero hour. The tese compound was suspended in 3% preboiled starch at 50 mg/ml. The rat was put in a metabolism cage. The 0–5 hour urine was collected and urinary sodium and potassium were determined using a Beckman Astra 4. The results of this test on representative compounds of this invention appear in Table II.

TABLE II

Diuretic Activity in Spontaneously Hypertensive Rats

| Compound | Volume ml | Sodium MEQ/5 Hours | Potassium MEQ/5 Hours |
|---|---|---|---|
| [[2-[(Dimethylamino)-methyl] phenyl]diphenyl-phosphoranylidene] carbamic acid, ethyl ester | 15.5 | 1.47 | 0.67 |
| [[2-[(Dimethylamino)-methyl] phenyl]diphenyl-phosphoranylidene] carbamic acid, methyl ester | 19.5 | 1.62 | 0.83 |
| [Diphenyl[2-(1-piperi-dinylmethyl)phenyl]-phosphoranylidene]carbamic acid, ethyl ester | 18.8 | 1.92 | 0.37 |
| [[2-[(Diethylamino)-methyl] phenyl]diphenyl-phosphoranylidene] carbamic acid, ethyl ester | 23.3 | 2.46 | 0.48 |
| [Diphenyl[2-(1-pyrroli-dinylmethyl)phenyl]-phosphoranylidene]carbamic acid, ethyl ester | 12.0 | 1.36 | 0.56 |
| [[2-[(Dipropylamino)-methyl] phenyl]diphenyl-phosphoranylidene] carbamic acid, ethyl ester | 22.0 | 1.41 | 0.40 |
| [[2-[(Methylamino)-methyl] phenyl]diphenyl-phosphoranylidene] carbamic acid, ethyl ester, monohydrochloride | 17.5 | 1.66 | 0.51 |

The compounds of the present invention have been found to be highly useful for lowering plasma renin activity, as diuretics and as cardiotonic agents in mammals when administered in amounts ranging from about 1.0 mg to about 50 mg/kg of body weight per day. A preferred dosage regimen for optimum results would be from about 3.0 mg to about 20.0 mg/kg of body weight per day. Such dosage units are employed that a total of from about 200 mg to about 1400 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular or subcutaneous routes, in appropriate quantities.

The active compounds of the present invention may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or organge flavor. Of course, any material used in preparing these dosage unit forms must be pharmaceutically pure and non-toxic.

The invention will be described in greater detail in conjunction with the following non-limiting examples.

EXAMPLE 1

[[2-[(Dimethylamino)methyl]phenyl]diphenylphosphoranylidene]carbamic acid, ethyl ester A 15.0 ml portion of N,N-dimethylbenzenemethanamine and 300 ml of ether were mixed under a nitrogen atmosphere. A 58 ml portion of 2.6M butyl lithium in hexane was added and this mixture was stirred, under nitrogen for 30 hours. A mixture of 27.0 ml of diphenylphosphine chloride in 60 ml of ether was added dropwise and the mixture was stirred overnight. Water was added, the organic layer was separated and extracted twice with dilute hydrochloric acid. The combined acid extracts were basified with 10% sodium hydroxide, then extracted twice with ether. The ether extracts were combined, dried and evaporated, giving 15.9 of 2-(diphenylphosphino)-N,N-dimethylbenzenemethanamine as an oil.

A 1.0 g of portion of this compound was added to 30 ml of ether and stirred. This solution was treated with 4.5 ml of 1m ethyl carbonazidate in ether. The mixture was allowed to stand 48 hours, then repeatedly concentrated and finally treated with fresh ether and refrigerated giving 770 mg of the product of the example, mp 103°–105° C.

EXAMPLE 2

[[2-[(Dimethylamino)methyl]phenyl]diphenylphosphoranylidene]carbamic acid, methyl ester A 2.0 g portion of 2-(diphenylphosphino)-N,N-dimethylbenzenemethanamine was reacted with 4.0 ml of 1M methyl carbonazidate in ether as described in Example 1, giving 1.32 g of the desired product, mp 95°–97° C.

EXAMPLE 3

[Diphenyl[2-(1-piperidinylmethyl)phenyl]phosphoranylidene]carbamic acid, ethyl ester A mixture of 11.9 ml of benzyl bromide in 100 ml of ether was added dropwise to a solution of 29.6 ml of piperidine in 100 ml of ether. This mixture was stirred overnight, then filtered. The organic layer was washed with water, then dried and concentrated to an oil. The oil was distilled through a Kugelrohr and the fraction boiling at 75°–85° C., 1.55 mm collected, giving 16.77 g of 1-(phenylmethyl)piperidine as an oil.

An 8.77 g portion of 1-(phenylmethyl)piperidine was mixed with 200 ml of ether under argon. A 27 ml portion of 2.6N butyl lithium in hexane was added, this mixture was allowed to stand one hour, then a solution of 12.6 ml of diphenylphosphine chloride in 50 ml of ether was added dropwise. This mixture was stirred 48 hours, then the ether layer was separated, washed with water, then extracted twice with 100 ml of water containing 8 ml of hydrochloric acid followed by water. The aqueous extracts were combined, basified with 12 ml of 10N sodium hydroxide and extracted twice with ether. The ether extracts were combined and concentrated, giving 15.5 g of diphenyl[2-(1-piperidinylmethyl)phenyl]phosphine as an oil.

A 5 g portion of the above compound was reacted with 15 ml of 1M ethyl carbonazidate in ether as described in Example 1, giving 1.9 g of the desired product, mp 121°–123° C.

EXAMPLE 4

[[[2-(Diethylamino)methyl]phenyl]diphenylphosphoranylidene]carbamic acid, ethyl ester A mixture of 11.9 ml of benzyl bromide in 100 ml of ether was added dropwise to a mixture of 30.9 ml of diethylamine in 100 ml of ether. This mixture was stirred overnight then filtered and washed with ether. The combined filtrate and wash was washed with water, dried and concentrated to an oil. This oil was distilled through a Kugelrohr and the fraction boiling at <70° C., 1.5 mm collected, giving 10.6 g of N,N-diethylbenzenemethanamine as an oil.

This oil was reacted with butyl lithium and diphenylphosphine chloride as described in Example 3, giving 19.8 g of oil, a portion of which was purified by chromatography giving 700 mg of [[2-(diethylamino)methyl]phenyl]diphenylphosphine as an oil.

A 600 mg portion of this oil was reacted with 4 ml of 1M ethyl carbonazidate in ether as described in Example 1, giving 400 mg of the desired product, mp 77°–84° C.

EXAMPLE 5

[Diphenyl[2-(1-pyrrolidinylmethyl)phenyl]phosphoranylidene]carbamic acid, ethyl ester A 25.0 ml portion of pyrrolidine was reacted with 10.9 ml of benzyl bromide in ether as described in Example 3, giving 12.3 g of 1-(phenylmethyl)pyrrolidine, which was then reacted with butyl lithium and diphenylphosphine chloride as described in Example 3, giving diphenyl]2-(1-pyrrolidinylmethyl)phenyl]phosphine.

A 1.0 g portion of this compound was purified by chromatography and 650 mg of the purified compound was reacted with 4 ml of 1M ethyl carbonazidate in ether as described in Example 1, giving 500 mg of the desired product, mp 120°–122° C.

EXAMPLE 6

[[2-[(Dipropylamino)methyl]phenyl]diphenylphosphoranylidene]carbamic acid, ethyl ester An 11.9 ml portion of benzyl bromide and 41 ml of dipropylamine in ether were reacted as described in Example 3, giving 17.6 g of N,N-dipropylbenzenemethanamine as a clear liquid.

A 9.56 g portion of the above compound was reacted with butyl lithium and diphenylphosphine chloride in ether as described in Example 3, giving 3.3 g of 2-(diphenylphosphino)-N,N-dipropylbenzenemethanamine as a viscous oil.

A 1.0 portion of this compound was then reacted with 6 ml of ;b 1M ethyl carbonazidate in ether as described in Example 1, giving 680 mg of the desired product, mp 102°-104° C.

EXAMPLE 7

[[2-[(Methylamino)methyl]phenyl]diphenylphosphoranylidene]carbamic acid, ethyl ester, monohydrochloride To a solution of 50.0 g of 2-bromobenzaldehyde in 50 ml of toluene was added ;b 25.0 ml of ethylene glycol plus 500 mg of p-toluenesulfonic acid. The mixture was heated at reflux with a Dean Stark Trap for 18 hours. Then an additional 10 ml of ethylene glycol was added to the mixture and reflux was continued for 4 hours longer. The solvent was evaporated in vacuo and the residue was dissolved in ether. The organic solution was washed with 5% sodium bicarbonate, dried over magnesium sulfate and filtered. The filtrate was evaporated to an oil which was distilled through a Kugelrohr apparatus. The fraction boiling at 130° C., 0.1 mm was collected giving 60.3 g of 2-(2-bromophenyl)-1,3-dioxolane.

A solution of 45.8 g of the preceding compound in 125 ml of ether was added dropwise to 5.5 g of magnesium in 150 ml of ether. The mixture was stirred and heated under argon with a few iodine crystals then agitated by sonication for 18 hours. The ether was boiled off and replaced with 150 ml of tetrahydrofuran. The mixture was heated to 50° C. and remained exothermic to completion. After 3 hours the mixture was cooled in an ice bath and 36 ml of diphenylphosphine chloride diluted with 12 ml of dry tetrahydrofuran was added over a 30 minute period. The mixture was heated at 40° C. for 2 hours then cooled in an ice/salt bath. Then 250 ml of a concentrated solution of ammonium chloride was added portionwise over a 30 minute period. The layers were separated and the aqueous layer was extracted twice with 250 ml portions dichloromethane. The dichloromethane extracts and the above tetrahydrofuran layer were combined and dried over magnesium sulfate. The mixture was filtered and the filtrate was evaporated to give a yellow cloudy syrup. The syrup was extracted with 500 ml of boiling ether. The extract was cooled to give pale yellow crystals. The crystals were collected and recrystallized from acetone to give 11.3 g of [2-(1,3-dioxolan-2-yl)phenyl]diphenylphosphine oxide, mp 161°-162° C.

A mixture of 11.0 g of the preceding compound in 500 ml of acetone was heated to the reflux temperature. Then several crystals of p-toluenesulfonic acid were added and the mixture was refluxed for 20 hours. The solvent was evaporated to give an oil which crystallized. The crystals were triturated with ether and filtered to give 5.3 g of 2-(diphenylphosphinyl)benzaldehyde as pale yellow crystals, mp 131°-134° C.

A 5.0 g amount of the preceding compound in 75 ml of ethanol was treated by bubbling in methylamine, then the solvent was evaporated to give a yellow syrup. The syrup was dissolved in 50 ml of toluene then crystals of p-toluenesulfonic acid were added. The mixture was heated at reflux for 2 hours while bubbling in methylamine. The mixture was evaporated to give a syrup, then 50 ml of ethanol was added plus about 200 mg of sodium borohydride. The mixture was stirred at room temperature for 16 hours. The solvent was evaporated in vacuo and a mixture of chloroform and water was added to the residue with stirring for 3 hours. The layers were separated and the aqueous layer was extracted once with chloroform. The chloroform solutions were combined, dried over magnesium sulfate, filtered and evaporated to give an oil. The oil dissolved in chloroform was treated with 2.5N hydrochloric acid. The chloroform layer was then washed with saturated sodium bicarbonate and dried. The chloroform solution was chromatographed on silica gel to remove about 200 mg of front running material. Then the column was washed with methanol and the eluate was collected and evaporated to give 4.1 g of yellow oil. The oil was extracted with 250 ml ether. The extracts were filtered through diatomaceous earth and allowed to evaporate at room temperature to give 4.0 g of the compound 2-(diphenylphosphinyl)-N-methylbenzenemethanamine as crystals, mp 71°-73° C.

A mixture of 4.0 g of the preceding product, 50 ml of toluene and 20 ml of trichlorosilane was heated at reflux for 24 hours. The mixture was evaporated to a syrup. Water and chloroform were added and the mixture was stirred with formation of a colorless prcipitate. The mixture was filtered to removed the precipitate which was washed with chloroform. The chloroform filtrate and wash was combined, dried over magnesium sulfate, filtered and evaporated to give 4.0 g of froth. This material was dissolved in 100 ml of dichloromethane. A 50 ml aliquot of this solution was treated with 15.0 ml of 1M ethyl carbonazidate in ether. The mixture was allowed to stand for 3 hours then was evaporated to a syrup. The syrup was treated with ethanol/ether to provide 1.4 g of crystals. Recrystallization from ethanol gave 190 mg of the product of the example, mp 151°-152° C.

EXAMPLE 8

Preparation of Compressed Tablet

| Ingredient | mg/Tablet |
|---|---|
| [[2-[(Dimethylamino)methyl]phenyl]diphenylphosphoranylidene]carbamic acid, ethyl ester | 5–100 |
| Dibasic calcium phosphate NF | qs |
| Starch USP | 40 |
| Modified starch | 10 |
| Magnesium stearate USP | 1–5 |

EXAMPLE 9

Preparation of Hard Shell Capsule

| Ingredient | mg/Capsule |
|---|---|
| [[2-[(Dipropylamino)methyl]phenyl]diphenylphosphoranylidene]carbamic | 5–100 |

| Ingredient | mg/Capsule |
|---|---|
| acid, ethyl ester | |
| Lactose, spray dried | qs |
| Magnesium stearate | 1–10 |

EXAMPLE 10

Intravenous Solutions

An organic acid such as citric, succinic, tartaric or mixtures thereof is dissolved in water at a concentration of 0.1–0.75%. [[2-[(Methylamino)methyl]phenyl]diphenylphosphoranylidene]carbamic acid, ethyl ester, monohydrochloride is dissolved in the acid-water mixture providing a clear solution which, after sterilization, is suitable for intravenous administration.

EXAMPLE 11

Intramuscular Preparation

[[2-[(Methylamino)methyl]phenyl]diphenylphosphoranylidene]carbamic acid, ethyl ester, monohydrochloride is dissolved in one of the following solvents or cosolvents and then sterilized, providing solutions for intramuscular administration.

| | |
|---|---|
| Benzyl alcohol | |
| Olive oil | |
| Peanut oil | |
| Propylene glycol/water | 20–80% |
| Polyethylene glycol 300/water | 20–100% |
| Polyethylene glycol 400/water | 20–100% |
| Polyethylene glycol 4000/water | 0.2–0.5% |
| Ethanol/water | 20–50% |

EXAMPLE 12

Oral Preparations

[[2-(Diethylamino)methyl]phenyl]diphenylphosphoranylidene]carbamic acid, ethyl ester is dissolved in one of the following systems providing solutions or suspensions for oral administration.

| | |
|---|---|
| Sodium lauryl sulfate/water | 0.5–3% |
| Polysorbate 80/water | 0.5–5% |
| Polysorbate 40/water | 0.01–0.75% |
| Polysorbate 20/water | 0.005–0.02% |
| Polyoxyethylene lauryl ether/water | 0.5–4% |
| Polyoxyethylene stearyl ether/water | 0.5–4% |
| Polyoxyethylene oleyl ether/water | 0.5–4% |

EXAMPLE 13

Oral Suspension

The following formulation provides an acceptable oral suspension.

| | |
|---|---|
| [[2-[(Methylamino)methyl]phenyl]diphenylphosphoranylidene]carbamic acid, ethyl ester, monohydrochloride | 1–5% |
| Veegum | 0.1–2.0% |
| Methyl paraben | 0.08% |
| Propyl paraben | 0.02% |
| Sucrose/Sorbitol | 20–80% |
| Flavor | qs |
| Water qs to | 100% |

We claim:

1. A compound of the formula:

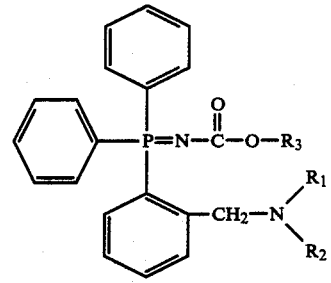

wherein $R_1$ and $R_2$ may be the same or different and are each individually hyrogen or lower alkyl having from one to four carbon atoms, where lower alkyl may include both straight chain and branched chain alkyl radicals; and $R_3$ is lower alkyl having from one to four carbon atoms.

2. The compound according to claim 1, [[2-[(dimethylamino)methyl]phenyl]diphenylphosphoranylidene]carbamic acid, ethyl ester.

3. The compound according to claim 1, [[2-[(dimethylamino)methyl]phenyl]diphenylphosphoranylidene]carbamic acid, methyl ester.

4. The compound according to claim 1, [[[2-(diethylamino)methy]phenyl]diphenylphosphoranylidene]-carbamic acid, ethyl ester.

5. The compound according to claim 1, [[2-[(dipropylamino)methyl]phenyl]diphenylphosphoranylidene]carbamic acid, ethyl ester.

6. The compound according to claim 1, [[2-[(methylamino)methyl]phenyl]diphenylphosphoranylidene]carbamic acid, ethyl ester, monohydrochloride.

7. A method for effecting diuresis in a mammal which comprises administering to the mammal a diuretic effective amount of a compound of the formula:

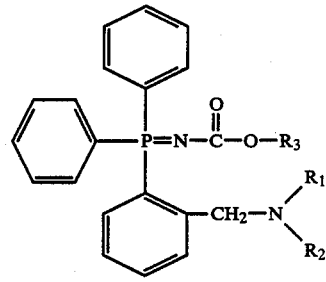

wherein $R_1$ and $R_2$ may be the same or different and are each individually hyrogen or lower alkyl having from one to four carbon atoms, where lower alkyl may include both straight chain and branched chain alkyl radicals; and $R_3$ is lower alkyl having from one to four carbon atoms.

8. A method for lowering plasma renin activity in a mammal which comprises administering to the mammal a plasma renin lowering amount of a compound of the formula:

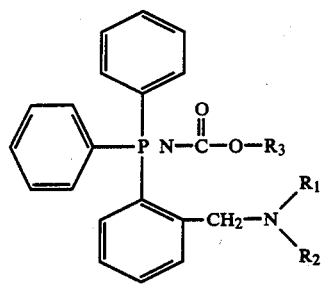

wherein $R_1$ and $R_2$ may be the same or different and are each individually hyrogen or lower alkyl having from one to four carbon atoms, where lower alkyl may include both straight chain and branched chain alkyl radicals; and $R_3$ is lower alkyl having from one to four carbon atoms.

9. A pharmaceutical composition of matter in dosage unit form comprising from about 10 mg to 500 mg of a compound of the formula:

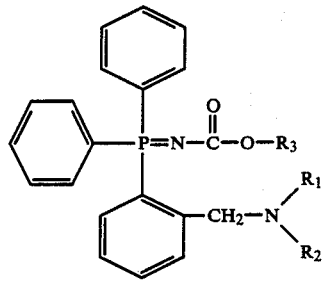

wherein $R_1$ and $R_2$ may be the same or different and are each individually hydrogen or lower alkyl having from one to four carbon atoms, where lower alkyl may include both straight chain and branched chain alkyl radicals; and $R_3$ is lower alkyl having from one to four carbon atoms, and a pharmaceutically acceptable carrier.

* * * * *